(12) United States Patent
Shores et al.

(10) Patent No.: US 7,736,358 B2
(45) Date of Patent: Jun. 15, 2010

(54) ELECTROSURGICAL GENERATOR AND METHOD FOR SIMULATING OUTPUT SIGNALS

(75) Inventors: Ronald B. Shores, Greenwood Village, CO (US); Brian C. Stuebe, Broomfield, CO (US)

(73) Assignee: ConMed Corporation, Utica, NY (US)

( * ) Notice: Subject to any disclaimer, the term of this patent is extended or adjusted under 35 U.S.C. 154(b) by 926 days.

(21) Appl. No.: 11/541,880

(22) Filed: Oct. 2, 2006

(65) Prior Publication Data

US 2008/0082096 A1 Apr. 3, 2008

(51) Int. Cl.
*A61B 18/04* (2006.01)
(52) U.S. Cl. .......................................... 606/34; 606/38
(58) Field of Classification Search ............. 606/32–38, 606/20–52; 307/17, 83, 68; 322/24, 28; 361/35, 91.1, 93.5, 93.6; 363/171, 157
See application file for complete search history.

(56) References Cited

U.S. PATENT DOCUMENTS

| | | | | |
|---|---|---|---|---|
| 4,032,726 A | * | 6/1977 | Chambers, Jr. | 379/400 |
| 4,037,066 A | * | 7/1977 | Kiko | 379/400 |
| 6,830,569 B2 | * | 12/2004 | Thompson et al. | 606/34 |
| 6,942,660 B2 | * | 9/2005 | Pantera et al. | 606/34 |
| 7,548,028 B2 | * | 6/2009 | Ushijima | 315/244 |
| 2005/0197657 A1 | * | 9/2005 | Goth et al. | 606/41 |

* cited by examiner

*Primary Examiner*—Linda C Dvorak
*Assistant Examiner*—Amanda Scott
(74) *Attorney, Agent, or Firm*—John R. Ley

(57) ABSTRACT

Voltage and current of an electrosurgical output signal which is conducted by a transformer are accurately simulated by executing a simulation algorithm to compensate for inherent distortion in the values of the current and voltage induced between primary and secondary windings of the transformer. The simulation algorithm is executed in response to voltage and current signals from a primary winding of the transformer, which may be a power output transformer or part of an electrosurgical output signal sensor.

35 Claims, 8 Drawing Sheets

$$V_{OUT}(S) = \frac{(K_{snv1}S^2 + K_{snv2}S + K_{snv3})}{(K_{sndv1}S^2 + K_{sdv2}S + K_{sdv3})} V_{IN}(S) + \frac{(K_{sni1}S^2 + K_{sni2}S + K_{sni3})}{(K_{sdi2}S + K_{sdi3})} I_{IN}(S)$$

136 ⤴

WHERE:

$K_{snv1} = L_{ls} \cdot R_{ser/shunt} \cdot C_{series} + N^2 \cdot L_{mag} \cdot R_{ser/shunt} \cdot C_{series}$ $K_{snv2} = N^2 \cdot R_{mag} \cdot R_{ser/shunt} \cdot C_{series} + R_{ls} \cdot R_{ser/shunt} \cdot C_{series} + N^2 \cdot L_{mag} + L_{ls}$ $K_{snv3} = R_{ser/shunt} + R_{ls} + N^2 \cdot R_{mag}$ $K_{sdv1} = N \cdot L_{mag} \cdot R_{ser/shunt} \cdot C_{series}$ $K_{sdv2} = N \cdot L_{mag} + N \cdot R_{mag} \cdot R_{ser/shunt} \cdot C_{series}$ $K_{sdv3} = N \cdot R_{mag}$ $K_{sni1} = L_{ls} \cdot R_{ser/shunt} \cdot C_{series}$ $K_{sni2} = L_{ls} + R_{ls} \cdot R_{ser/shunt} \cdot C_{series}$ $K_{sni3} = R_{ser/shunt} + R_{ls}$ $K_{sdi2} = N \cdot R_{ser/shunt} \cdot C_{series}$ $K_{sdi3} = N$

FIG.4

$$V_{OUT}(Z) = \frac{(K_{znv1}Z^2 + K_{znv2}Z + K_{znv3})}{(K_{zdv1}Z^2 + K_{zdv2}Z + K_{zdv3})} V_{IN}(Z) + \frac{(K_{zni1}Z^2 + K_{zni2}Z + K_{zni3})}{(K_{zdi1}Z^2 + K_{zdi2}Z + K_{zdi3})} I_{IN}(Z)$$

$$V_{OUT}[n] = \frac{K_{znv1}}{K_{zdv1}} V_{IN}[n] + \frac{K_{znv2}}{K_{zdv1}} V_{IN}[n-1] + \frac{K_{znv3}}{K_{zdv1}} V_{IN}[n-2] + ...$$

$$\frac{K_{zni1}}{K_{zdi1}} I_{IN}[n] + \frac{K_{zni2}}{K_{zdi1}} I_{IN}[n-1] + \frac{K_{zni3}}{K_{zdi1}} I_{IN}[n-2] + ...$$

$$- (K_{zdv2} + K_{zdi2}) V_{OUT}[n-1] - (K_{zdv3} + K_{zdi3}) V_{OUT}[n-2]$$

FIG. 8

$$I_{OUT}(z) = \frac{(C_{znv0}z^3 + C_{znv1}z^2 + C_{znv2}z + C_{znv3})}{(C_{zdv0}z^3 + C_{zdv1}z^2 + C_{zdv2}z + C_{zdv3})} V_{IN}(z) + \frac{(C_{zni0}z^3 + C_{zni1}z^2 + C_{zni2}z + C_{zni3})}{(C_{zdi0}z^3 + C_{zdi1}z^2 + C_{zdi2}z + C_{zdi3})} I_{IN}(z)$$

$\swarrow$ 146

FIG. 9

$\Big\}$ 64

$$I_{OUT}[n] = \left(\frac{C_{znv0}}{C_{zdv0}}\right) V_{IN}[n] + \left(\frac{C_{znv1}}{C_{zdv0}}\right) V_{IN}[n-1] + \left(\frac{C_{znv2}}{C_{zdv0}}\right) V_{IN}[n-2] + \left(\frac{C_{znv3}}{C_{zdv0}}\right) V_{IN}[n-3] + \left(\frac{C_{zni0}}{C_{zdi0}}\right) I_{IN}[n] + \left(\frac{C_{zni1}}{C_{zdi0}}\right) I_{IN}[n-1] + \ldots$$

$$+ \left(\frac{C_{zni2}}{C_{zdi0}}\right) I_{IN}[n-2] + \left(\frac{C_{zni3}}{C_{zdi0}}\right) I_{IN}[n-3] - (C_{zdv1} + C_{zdi1})I_{OUT}[n-1] - (C_{zdv2} + C_{zdi2})I_{OUT}[n-2] - (C_{zdv3} + C_{zdi3})I_{OUT}[n-3]$$

$\swarrow$ 147

FIG. 10

$$V_{OUT}(z) = \frac{(K_{znv0}z^3 + K_{znv1}z^2 + K_{znv2}z + K_{znv3})}{(K_{zdv0}z^3 + K_{zdv1}z^2 + K_{zdv2}z + K_{zdv3})} V_{IN}(z) + \frac{(K_{zni0}z^3 + K_{zni1}z^2 + K_{zni2}z + K_{zni3})}{(K_{zdi0}z^3 + K_{zdi1}z^2 + K_{zdi2}z + K_{zdi3})} I_{IN}(z)$$

$\swarrow$ 148

FIG. 11

$$V_{OUT}[n] = \left(\frac{K_{znv0}}{K_{zdv0}}\right) V_{IN}[n] + \left(\frac{K_{znv1}}{K_{zdv0}}\right) V_{IN}[n-1] + \left(\frac{K_{znv2}}{K_{zdv0}}\right) V_{IN}[n-2] + \left(\frac{K_{znv3}}{K_{zdv0}}\right) V_{IN}[n-3] + \left(\frac{K_{zni0}}{K_{zdi0}}\right) I_{IN}[n] + \left(\frac{K_{zni1}}{K_{zdi0}}\right) I_{IN}[n-1] + \ldots$$

$$+ \left(\frac{K_{zni2}}{K_{zdi0}}\right) I_{IN}[n-2] + \left(\frac{K_{zni3}}{K_{zdi0}}\right) I_{IN}[n-3] - (K_{zdv1} + K_{zdi1})V_{OUT}[n-1] - (K_{zdv2} + K_{zdi2})V_{OUT}[n-2] - (K_{zdv3} + K_{zdi3})V_{OUT}[n-3]$$

$\swarrow$ 149

ELECTROSURGICAL GENERATOR AND METHOD FOR SIMULATING OUTPUT SIGNALS

CROSS REFERENCE TO RELATED APPLICATION

This invention is related to an invention for a Near-instantaneous Responsive Closed Loop Control Electrosurgical Generator and Method, described in U.S. patent application Ser. No. 11/541,819, filed concurrently herewith by the present inventors and assigned to the assignee of the present invention. The disclosure of this concurrently-filed U.S. patent application is incorporated herein by this reference.

FIELD OF THE INVENTION

This invention relates to electrosurgery, and more specifically, to a new and improved electrosurgical generator and method for accurately and rapidly simulating electrosurgical output waveforms and signals applied to the tissue during electrosurgery. Even more particularly, the present invention relates to simulating electrosurgical output signals from voltage and current signals applied to a primary winding of an electrosurgical power output transformer.

BACKGROUND OF THE INVENTION

In broad terms, electrosurgery is the application of a high-voltage, high-frequency (HF) or radio-frequency (RF) output waveform to tissue to achieve a surgical effect. Tissue is cut, coagulated by stopping blood flow, or simultaneously cut and coagulated, depending upon the electrical characteristics of the electrosurgical output waveform. To achieve cutting, the output signal is substantially continuous. To achieve coagulation, the output signal is delivered in bursts with each burst defined by a duty cycle in which the on-time of the duty cycle is substantially less in time duration than the off-time. To achieve simultaneous cutting and coagulation, the output signal is also delivered in bursts, but the on-time and the off-time of the duty cycle are comparable in time to each other, or the on-time may exceed the off-time. The electrosurgical output signal is delivered to the tissue from an active electrode of an applicator or handpiece that is manipulated by the surgeon. The electrosurgical output signal is conducted to the active electrode over a conductor extending from the electrosurgical generator to the applicator or handpiece.

Accurate knowledge of the voltage and current characteristics of the electrosurgical output signal is important for controlling and monitoring the power applied to the tissue, or for monitoring other parameters related to or derived from the electrosurgical output voltage and current, such as impedance. The output voltage and current values may also be monitored to ensure that they stay within desired operating limits, for example. Data describing the electrosurgical output signals may also be collected when monitoring a surgical procedure.

The load into which the electrosurgical output signal is delivered varies substantially during a surgical procedure due to large and almost instantaneous changes in the point-to-point resistance or impedance of the tissue encountered. For example, a highly fluid-perfused tissue, such as the liver, may exhibit a resistance or impedance in the neighborhood of 10-20 ohms while other tissues, such as skin or bone marrow, may have an impedance in the neighborhood of 1000 to 2000 ohms. When the active electrode passes from low impedance tissue into high impedance tissue, less current is momentarily delivered to the high impedance tissue thereby immediately degrading or inhibiting the desired electrosurgical effect. On the other hand, when the active electrode passes from high impedance tissue into low impedance tissue, high current is momentarily delivered into the low impedance tissue and that high current may create excess tissue damage. The variable impedance characteristics of the tissue require the electrosurgical generator to deliver and control relatively wide variations of power on a rapidly-changing basis.

The common technique of monitoring the voltage and current of an electrosurgical output signal is to connect output voltage and current sensors to the conductor extending from the electrosurgical generator to the handpiece or applicator. These sensors develop output current and output voltage sense signals corresponding to the actual output current and voltage applied to the tissue. However, the output sensors impose additional capacitive, resistive and/or inductive loads on the electrosurgical output signal, thereby changing its output characteristics. The load from these sensors decreases the amount of power reaching the tissue and increases leakage current. Leakage current is current which flows into the surrounding environment other than into the tissue at the surgical site. Leakage current can cause a lack of accuracy in output power regulation, or be a source of unintended patient burns and hazards to operating room personnel. The output voltage sensors must have the capability of withstanding high output voltage, and therefore the sensors may be relatively costly.

Because of these and other problems with output voltage and current sensors, attempts have been made to regulate output power by using voltage and current sensors on the primary winding of a power output transformer of an electrosurgical generator. The power output transformer transforms the energy of the primary voltage and current signals supplied to the primary winding into the electrosurgical output signal which is supplied from the secondary winding of the transformer. If the power output transformer was an ideal electrical element, the voltage and current of the output signal would be directly related mathematically to the voltage and current at the primary winding by a constant multiplied by the ratio of the turns of the primary winding and of the secondary winding. However, these simple relationships are valid only for an ideal transformer, and an electrosurgical power output transformer is far from an ideal circuit element. Consequently, the voltage and current signals from the primary winding voltage and current sensors do not accurately represent the voltage and current of the output signal from the secondary winding in a typical electrosurgical power output transformer.

An electrosurgical power output transformer has a complex set of variable electrical characteristics which cause the output signal to be substantially different from the primary current and voltage signals. Parasitic capacitances between the windings and the core of the output transformer store and divert different amounts of energy at different frequencies, and therefore cause changes in the spectral energy content or bandwidth of the output signal compared to the input signals. Core losses consume energy from the primary signals, as do the resistances of the winding conductors. The core losses depend on the frequency component of the signals and the instantaneous value of the load presented by the tissue. The electrosurgical output signal, particularly in a spray coagulation mode of operation, use the energy storage characteristics of the inductance of the primary winding to delay the energy delivery to the output signal. Consequently, the relationships of the input signal to the output signal become phase shifted, frequency attenuated and frequency distorted relative to one another.

In those types of electrosurgical generators which rely on sensing the voltage and current at the primary winding of the output transformer, the sensed primary voltage and current values, which do not accurately represent the voltage and current of the output signal, are instead used as approximations. Those approximations do not provide the precision desired for accurate control and monitoring of the electrosurgical output signal applied to the patient.

Even in those cases where the output signals are sensed by output sensors, the signals supplied by the output sensors may not be processed quickly enough to be effective in precisely controlling the output power from an electrosurgical generator. A control loop time lag or phase lag, which is that time between acquiring the sensed signals and making an adjustment to the output signals, may be so long that a response cannot be achieved quickly enough to obtain or maintain the desired effect. The control loop time lag or phase lag is dependent upon many factors, but a principal factor relates to the speed at which the output voltage and current signals may be derived and processed into a usable feedback or other control signal. The same circumstance also applies with respect to monitoring the other output-related factors, such as tissue impedance, which must be calculated based on the output voltage and current signals that exist on an instantaneous basis.

SUMMARY OF THE INVENTION

The present invention accurately and rapidly simulates voltage and current values of an electrosurgical output signal supplied by an electrosurgical output waveform conducting transformer, using only the input current and voltage signals at the input winding of the transformer. The simulation is achieved by one or more mathematical algorithms which accurately simulate the output voltage and current signals based on the sensed values of the input voltage and current signals. The mathematical simulation algorithms may be derived using one or more known circuit analytical techniques, such as lumped parameter, equivalent circuit modeling or iterative numerical comparisons. The simulation mathematical algorithms are executed rapidly, preferably by use of an array of logic gates which logically combine the sensed signals representative of the voltage and current applied to the input winding of the transformer. Executing the simulation algorithm with an array of logic gates computes the simulated output signals very rapidly, since the simulated output signals are delayed relative to the sensed input signals only by gate and clocking delays associated with the logic gate array. Rapidly deriving the simulated output signals allows them to be applied immediately for controlling the electrosurgical generator, thereby achieving highly responsive feedback power control with a minimum of control loop lag time or phase lag. Rapid and precise power regulation is achieved. Enhanced monitoring of patient parameters, such as tissue impedance, is also achieved.

These and other advantages and improvements are obtained by an electrosurgical generator which supplies a high-frequency high-voltage output signal for application to tissue to create an electrosurgical effect. The electrosurgical generator includes a transformer having a primary winding and a secondary winding. The secondary winding conducts the output signal. The transformer induces voltage and current signals between the primary and secondary windings that are distorted relative to one another due to inherent electrical characteristics of the transformer at the high frequency of the output signal. A simulation circuit is connected to the primary winding to receive voltage and current signals which respectively represent the voltage and current of the primary winding. The simulation circuit executes a mathematical algorithm to transform at least one of the voltage and current signals received from the primary winding into at least one simulated signal. The simulated signal accurately represents a true value of one of voltage or current of the output signal conducted by the secondary winding of the transformer. The transformation of the one of the voltage and current signals by the simulation algorithm compensates for the distortion of the transformer when the voltage and current signals are induced between the primary and secondary windings.

The advantages and improvements of the invention are also obtained by a method of accurately simulating at least one of voltage or current of an electrosurgical output signal sensed by a transformer which has inherent characteristics that distort the respective values of the current and voltage induced between primary and secondary windings of the transformer. The method involves executing a mathematical simulation algorithm on voltage and current signals representative of voltage and current received from the primary winding to transform at least one of the voltage and current signals from the primary winding into at least one simulated signal which accurately represents the true value of one of voltage or current of the output signal conducted by the secondary winding. The simulation algorithm also compensates for the distortion induced by the transformer.

Further aspects of the invention relate to deriving the mathematical simulation algorithm. The simulation algorithm may be derived from a lumped parameter, equivalent circuit model of the transformer upon which mathematical processing has been performed, or from other system identification techniques based on iteratively comparing on the voltage and current signals from the primary winding and the voltage and current of the output signal. The simulation algorithm also comprises a mathematical function which supplies the simulated signal from a first variable formed by the voltage from the primary winding, a second variable formed by the current from the primary winding, and a set of coefficients determined by an iterative numerical comparison of the voltage and current signals from the primary winding and the voltage and current of the output signal. The set of coefficients can also be determined from an equivalent circuit model of the transformer. The mathematical algorithm is preferably executed by an array of logic gates, with the computation of the simulated signal delayed only by the time consumed by gate and calculation clocking delays of the array of logic gates.

While the transformer may be used for different purposes in an electrosurgical generator, the transformer may constitute all or part of an output transformer which transforms energy delivered to the primary winding into the electrosurgical output signal. The transformer may also constitute part of a sensor connected to conduct the output signal and derive a sense signal related to the electrosurgical output signal.

A more complete appreciation of the present invention and its scope, and the manner in which it achieves the above and other improvements, can be obtained by reference to the following detailed description of presently preferred embodiments taken in connection with the accompanying drawings, which are briefly summarized below, and the appended claims.

BRIEF DESCRIPTION OF THE DRAWINGS

FIGS. 4-6 show equations employed in determining the simulation algorithm from the equivalent circuit shown in FIG. 3.

FIGS. 8-11 show equations employed in determining the simulation algorithm from the analytical circuit model shown in FIG. 7.

DETAILED DESCRIPTION

Figure 1:
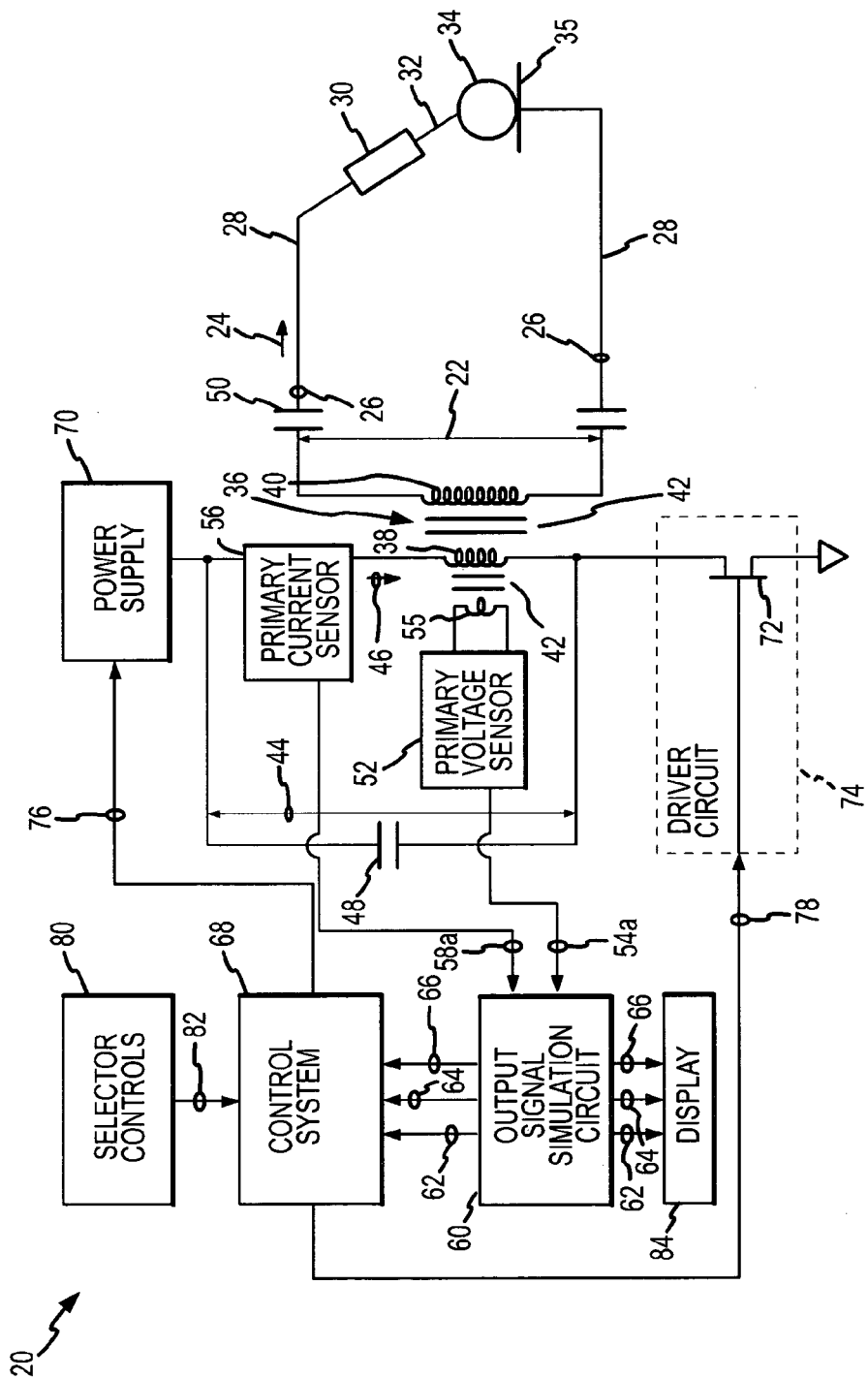
FIG. 1 is a block diagram of an electrosurgical generator incorporating the present invention.

An electrosurgical generator 20 which incorporates the present invention is shown in FIG. 1. The electrosurgical generator 20 creates and delivers an electrosurgical output signal formed by an output voltage 22 and an output current 24. The electrosurgical output signal is delivered from output terminals 26 of the generator 20 and is conducted over a lead or conductor 28 to an applicator or handpiece 30. The handpiece 30 includes an active electrode 32 through which the output voltage 22 and output current 24 are applied at a surgical site to tissue of a patient 34 by the surgeon manipulating the handpiece 30. A return electrode 35 is connected to the patient 34 a location remote from the surgical site. Another lead or conductor 28 connects the return electrode 35 to the electrosurgical generator 22 to complete an electrical circuit through the patient 34. When applied by the active electrode 32 to the tissue of the patient 34, the output voltage 22 and the output current 24 create a desired electrosurgical effect on the tissue, such as cutting, coagulating or simultaneous cutting and coagulating. Electrosurgical effects can also be achieved by combining comparably sized active and return electrodes in a single, hemostat-like bipolar instrument and gripping the tissue between the electrodes while conducting the electrosurgical voltage 22 and current 24 through the gripped tissue, as is well known in bipolar electrosurgery.

The electrosurgical generator 20 includes an output transformer 36 having a primary winding 38 and a secondary winding 40 which are wrapped in coils around a core 42 of magnetic material. The electrosurgical output signal of the output voltage 22 and output current 24 is induced into and supplied by the secondary winding 40 in response to the application of an input or primary voltage 44 and an input or primary current 46 applied to and conducted by the primary winding 38. A capacitor 48 is connected in parallel with the primary winding 38 to form a conventional resonant circuit with the primary winding 38. The resonant circuit creates oscillations of the voltage 44 and current 46 in the primary winding 38 at the natural frequency of the resonant circuit. The output voltage 22 and output current 24 oscillate in the secondary winding 40 at the same frequency as the natural frequency of the resonant circuit. The natural frequency of the resonant circuit therefore establishes the high or radio frequency of the output voltage 22 and the output current 24.

Isolating or blocking capacitors 50 are connected between the secondary winding 40 and the output terminals 26. The capacitors 50 isolate the patient 34 from the electrosurgical generator 20 but conduct the high frequency output voltage 22 and current 24 to the tissue of the patient 34. The isolating capacitors 50 are typically required by safety regulations governing electrosurgery to ensure that very low frequency galvanic currents do not flow into the patient.

The electrosurgical generator 20 includes a primary voltage sensor 52 to sense the magnitude of the primary voltage 44 oscillating in the resonant circuit. The primary voltage sensor 52 supplies a primary voltage sense signal 54a which represents the magnitude of the primary voltage 44 across the primary winding 38. The primary voltage sensor 52 preferably uses an additional sense winding 55 wound on the core 42 adjacent to the primary winding 38, or alternatively, the primary voltage sensor 52 may use part of the primary winding 38 as an autotransformer (not shown). A primary current sensor 56 is connected in series with the primary winding 38 in the resonant circuit. The primary current sensor 56 senses the magnitude of the primary current 46 flowing through the primary winding 38 and supplies a corresponding primary current sense signal 58a.

An important aspect of the electrosurgical generator 20 is an output signal simulation circuit 60. The output signal simulation circuit 60 receives the primary voltage sense signal 54a and the primary current sense signal 58a, and by using the signals 54a and 58a, executes one or more predetermined mathematical algorithms which accurately simulate the true values of the output voltage 22 and/or the output current 24 of the electrosurgical output signal at the secondary winding 40 of the transformer 36. The mathematical simulation algorithms compensate for the distortion created by the transformer 36 when the primary voltage and current signals 44 and 46 induce the secondary voltage and current signals 22 and 24.

The simulation circuit 60 avoids the need to connect separate current and voltage sensors to the secondary winding 40 of the output transformer 36 to obtain accurate values of the output voltage 22 and/or the output current 24 from the transformer 36. By avoiding the use of separate current and voltage sensors connected to the secondary winding 40 of the output transformer 36, the electrosurgical output waveform is not degraded by the effects of those sensors.

In addition, the output signal simulation circuit 60 also simulates the power of the output voltage and current signals 22 and 24. The primary voltage and current sense signals 54a and 58a are multiplied to calculate input power from which an estimate of the power losses of the transformer 36 are subtracted to arrive at the simulated electrosurgical power output. The output power can also be simulated by multiplying the simulated output voltage value and the simulated output current value after those values have been derived.

The simulation circuit 60 supplies a simulated output voltage signal 62, a simulated output current signal 64, and a simulated output power signal 66. Preferably, the simulation circuit 60 is implemented as an array of logic gates which, by their interoperative and programmable connections, rapidly and quickly perform the calculations involved in executing each simulation algorithm to create and obtain the simulated output signals 62, 64 and 66. Using an array of logic gates to perform these functions makes the simulated signals 62, 64 and 66 available for use very quickly. The availability of these simulated signals is delayed only by gate and computational clock delays. Gate and clock delays are considerably shorter in time than the calculation delays typically involved in other types of digital computations. The near-instantaneous availability of the simulated signals 62, 64 and 66 makes it very advantageous to use these simulated signals for obtaining precise feedback control of the power and other characteristics of the output waveform from the electrosurgical generator, without significant control loop lag time or phase lag.

The simulated output voltage, current and power signals 62, 64 and 66 are supplied to a control system 68 of the electrosurgical generator 20 to obtain feedback control. The control system 68 utilizes one or more of the simulated signals 62, 64 and 66 as a feedback signal for controlling the performance of the electrosurgical generator 20. The resonant circuit, formed by the primary winding 38 and the capacitor 48, is charged with electrical energy from a power supply 70 when a switch 72 of a driver circuit 74 is conductive. The control system 68 adjusts the power supply 70 by supplying a control signal 76 to the power supply 70, thereby varying the energy delivered to the resonant circuit. The control system 68 also asserts a switch control signal 78 to the switch 72 of the driver circuit 74. The control system 68 adjusts the time width or on-time duration of the asserted switch control signal 78, or some other typical characteristic of the control signal 78, to thereby control the time duration during which the resonant circuit is charged with energy transferred from the power supply 70. The amount of energy which charges the resonant circuit is directly related to the time width or on-time duration of the asserted switch signal 78, or the other control characteristic of the signal 78.

In general, the switch 72 and the signal 78 is any power amplifier device and control signal that varies the energy transferred to the resonant circuit. Techniques for varying the energy transfer to the resonant circuit include a switch and a fixed frequency switch signal where the duty cycle on the switch signal varies the energy transfer, a switch and a fixed frequency switch signal where the supply voltage to the resonant circuit varies the energy transfer, a switch and a fixed pulse width switch signal where the pulse repetition frequency varies the energy transfer, a switch and a fixed pulse width switch signal where the supply voltage to the resonant circuit varies the energy transfer, a switch and a fixed frequency and fixed pulse width switch signal where varying the saturation voltage of the switch varies the energy transferred, and a magnetic amplifier and a variable saturation threshold signal to an inductor which varies the energy transferred, among other things.

When the switch control signal 78 is deasserted and the switch 72 of the driver circuit 74 ceases conducting, the energy transferred into the resonant circuit commences oscillating at the natural frequency of the resonant circuit, causing the primary voltage signal 44 and the primary current signal 46 to alternate at that natural frequency. The transformer 36 induces the output voltage 22 and output current 24 of the electrosurgical output signal from the energy oscillating in the resonant circuit. Since a significant amount of the energy in the resonant circuit is transferred by the output transformer 36 into the electrosurgical output signal formed by the output voltage 22 and the output current 24, the amount of energy of the electrosurgical output signal is controlled and adjusted by varying the time width of the on-time, or other characteristics, of the asserted switch signal 78 and by adjusting or controlling the power supply 70.

The electrosurgical generator 20 also includes conventional selector controls 80 which are connected to the control system 68. The selector controls 80 include selection switches (not shown) which allow the power content of the output signal to be selected and which allow the mode of operation of the electrosurgical generator to be selected. The modes of operation are cutting, coagulation and simultaneous cutting and coagulation known as "blend." Selector signals 82 supplied by the selector controls 80 form the reference signal in a feedback control system, while one or more of the simulated signals 62, 64 and 66 form the response signals in a feedback control system. The difference between one or more of the simulated output signals 62, 64 and 66 and the selector reference signals 82 constitutes a feedback error signal that is thereafter used to control the output power and/or other performance characteristics from the electrosurgical generator 20.

One or more of the simulated output signals 62, 64 and 66 may be displayed on a display 84 or otherwise made available for use by the electrosurgical generator 20 or by auxiliary equipment employed in an operating room in conjunction with the electrosurgical generator 20. For example, the display 84 may be part of an another type of control system for the electrosurgical generator which causes that electrosurgical generator to respond to a patient related parameter, such as impedance, which can be derived from dividing the simulated voltage and current signals 62 and 64.

Figure 2:
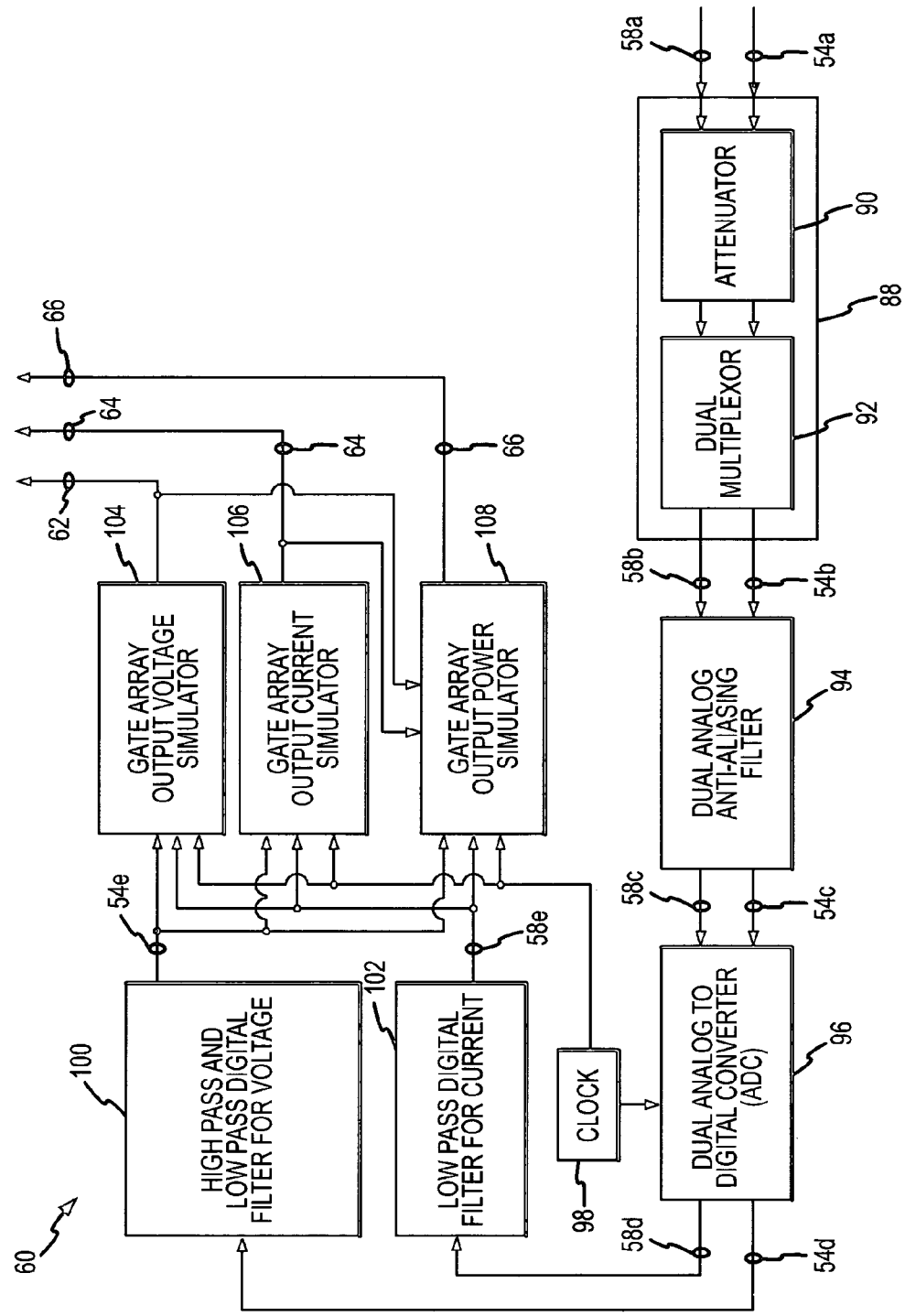
FIG. 2 is a block diagram of an output signal simulation circuit of the electrosurgical generator shown in FIG. 1.

More details of the output signal simulation circuit 60 and its relationship with the other components of the electrosurgical generator 20 are shown in FIG. 2. The primary voltage sense signal 54a and the primary current sense signal 58a are supplied to an attenuator bank 88. The attenuator bank 88 is formed by an attenuator 90 and a dual multiplexer 92. The attenuator 90 attenuates the magnitude of the primary voltage sense signal 54a and the primary current sense signal 58a. The dual multiplexer 92 is set prior to activation of the electrosurgical generator and therefore does not change the output terminal connections to which its input signals are supplied. Consequently, the attenuator 88 supplies an attenuated primary voltage sense signal 54b and an attenuated primary current sense signal 58b.

The attenuated voltage and current sense signals 54b and 58b are supplied to a dual analog anti-aliasing filter 94. The anti-aliasing filter 94 is a low pass filter that generates a filtered primary voltage sense signal 54c and a filtered primary current sense signal 58c, after undesired high frequency and higher order harmonic components have been removed from the attenuated signals 54b and 58b. The anti-aliasing filter 94 assures that the significant frequency components of the filtered signals 54c and 58c are below a predetermined upper frequency to prevent the creation of unintended aliased signals from the signals 54b and 58b, when the voltage and current sense signals are converted into digital signals.

The filtered signals 54c and 58c are supplied to a dual analog to digital converter (ADC) 96 which is driven by a clock 98. The dual ADC 96 and clock 98 determine the sampling and conversion rate of the filtered analog primary voltage sense signal 54c and the filtered analog primary current sense signal 58c. The dual ADC 96 converts the filtered signals 54c and 58c to a digital primary voltage sense signal 54d and a digital primary current sense signal 58d, respectively.

The digital primary voltage sense signal 54d is supplied to a high pass and low pass digital filter 100 with signal compensation. The filter 100 eliminates the effect of residual energy stored in the isolation capacitors 50 (FIG. 1) at the end of an activation of the electrosurgical generator. The energy stored in the isolation capacitors 50 can vary depending upon the technique of the surgeon and the mode of electrosurgical procedure. Without eliminating the effect of the residual stored energy in the capacitors 50, the output simulation is less accurate. After high and low pass filtering and compensation of the signal 54d, the high and low pass digital filter 100 supplies a filtered and compensated digital voltage signal 54e.

The digital primary current sense signal 58d is conducted to a low pass digital filter 102. The low pass filter 102 also prevents anti-aliasing. After low pass filtering the digital signal 58d, the low pass digital filter 102 supplies a filtered digital current signal 58e.

The digital voltage signal 54e and the digital current signal 58e are conducted to an output voltage simulator 104, to an output current simulator 106, and to an output power simulator 108. The simulators 104, 106 and 108 each respond to the signals 54e and 58e by executing mathematical simulation algorithms which simulate an accurate value of the output voltage 22 (FIG. 1), the output current 24 (FIG. 1) and the output power (associated with the output voltage 22 and the output current 24 (FIG. 1)), respectively. The accurate simulations are then supplied as the simulated voltage, current, and power signals 62, 64 and 66, respectively.

Preferably, each of the simulators 104, 106 and 108 is implemented as an array of logic gates. The logic gates have been programmed and interconnected to execute the mathematical simulation algorithm of each simulator. Using an array of logic gates to execute the mathematical algorithms results in producing and delivering the simulated signals 62, 64 and 66 very rapidly, since those simulated signals are delayed only by the very short gate delays and the calculation clocking delays associated with digital logic gates and not by other more time-consumptive computational delays.

Figure 3:
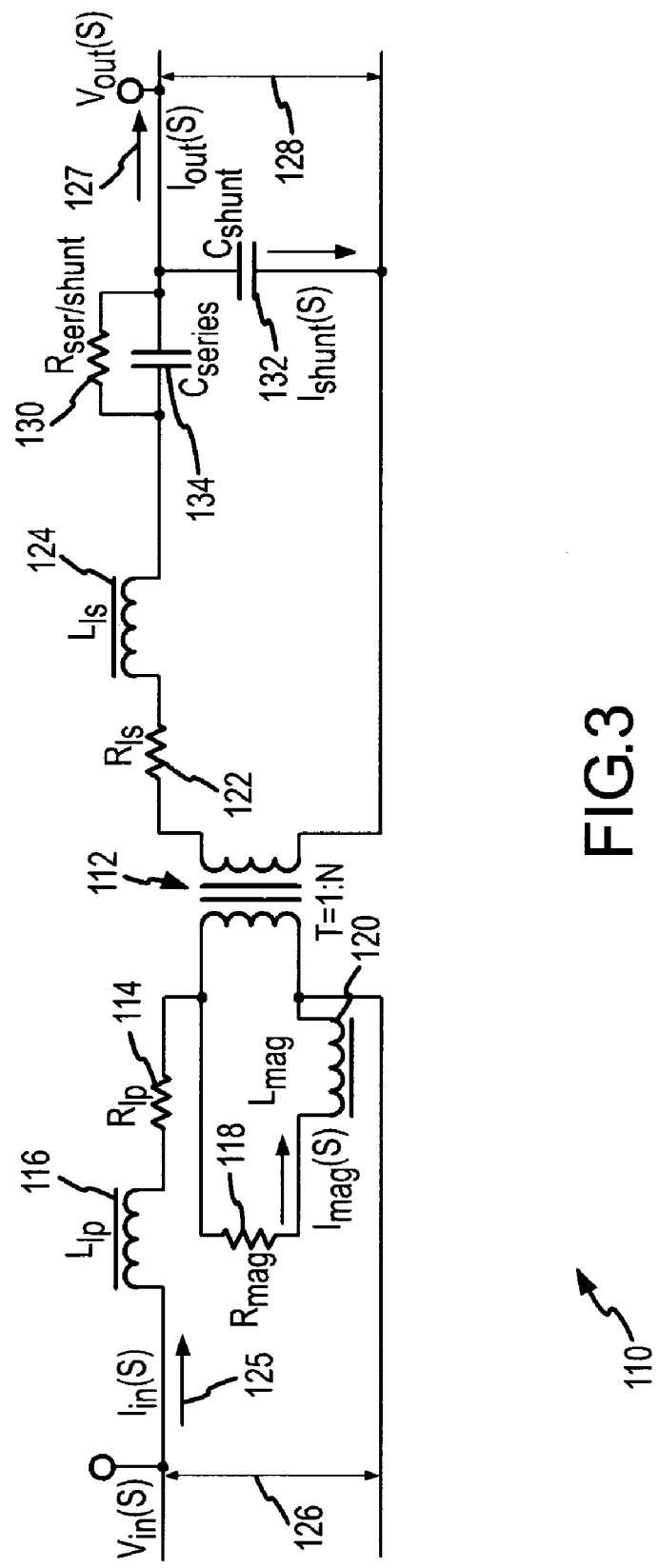
FIG. 3 is a lumped parameter equivalent circuit of an output circuit of the electrosurgical generator shown in FIG. 1, used to derive a simulation algorithm which is executed by a simulator of the output signal simulation circuit shown in FIG. 2.

A number of different known mathematical algorithms can be executed by the simulators 104, 106 and 108 to simulate accurate values of the output signal. One advantageous algorithm for simulating output voltage is derived from a model of a lumped parameter, equivalent circuit 110 of an output circuit of the electrosurgical generator 20 formed by the output transformer 36 and the isolation capacitors 50 (FIG. 1). One such lumped parameter, equivalent circuit 110 is shown in FIG. 3. The use of equivalent circuits to model the non-ideal behavior of electronic circuit components is known, and the equivalent circuit 110 is one of many possible equivalent circuits that could be used to derive a response function for the output transformer 36 and the isolation capacitors 50 (FIG. 1). It is important to establish lumped parameters for the equivalent circuit which can be measured from the actual transformer and isolation capacitors which the equivalent circuit 110 models, because the accuracy of those measured values establishes the accuracy of the equivalent circuit model as the basis for the simulation algorithm. All of the elements of the equivalent circuit 110 are assumed to be ideal.

The portion of the basic lumped parameter equivalent circuit 110 which relates to the output transformer 36 (FIG. 1) is formed by a transformer 112, a primary leakage resistor ($R_{lp}$) 114, a primary leakage inductor ($L_{lp}$) 116, a magnetic resistor ($R_{mag}$) 118, a magnetic inductor ($L_{mag}$) 120, a secondary leakage resistor ($R_{ls}$) 122, and a secondary leakage inductor ($L_{ls}$) 124.

The primary leakage resistor 114 and the secondary leakage resistor 122 model the resistance encountered by the AC current $I_{in}(s)$ 125 which is conducted through the primary winding and the AC current $I_{out}(s)$ 127 which is conducted through the secondary winding, respectively. The resistance encountered by these AC currents flowing through the windings 38 and 40 (FIG. 1) results in energy losses as heat, and these energy losses are commonly known as copper losses. The energy losses are reflected in a voltage drop from an input voltage $V_{in}(s)$ 126 to an output voltage $V_{out}(s)$ 128 of the equivalent transformer circuit 110.

The primary leakage inductor 116 and the secondary leakage inductor 124 model the flux leakage of the core 42 (FIG. 1). Leakage flux emanates from the core and fails to couple the primary winding 38 with the secondary winding 40 (FIG. 1). The inductors 116 and 124 in the equivalent circuit 110 introduce a phase shift between the current and voltage that is present at the windings 38 and 40 (FIG. 1). The effect of the phase shift is that the real power of the output signal delivered from the secondary winding 40 (FIG. 1) is diminished, because some of the apparent power is reactive power.

Real power and reactive power are combined through vector analysis (or a power triangle) to obtain apparent power. Only the real power produces an electrosurgical effect at the tissue of the patient 34 (FIG. 1). Reactive power does not produce an electrosurgical effect. The consumption of output power as reactive power may diminish the ability to achieve a desired electrosurgical effect, or may result in the storage of power in some types of electrosurgical accessories which is later released as real power under circumstances where an electrosurgical effect was not desired.

The magnetic resistor 118 account for core losses. To produce the magnetic flux within the core 42 (FIG. 1), an exciting current is required. The magnetic resistor 118, known as the core-loss resistance, accounts for the core-loss current, or the real component of the exciting current. The magnetic inductor 120, known as the magnetizing reactance, accounts for the magnetizing current in the core or the imaginary-component of the exciting current component.

The electrosurgical output signal of the output transformer 36 is a high or radio frequency signal (typically 350-600 kHz) that experiences rapidly changing transient conditions due to the highly variable impedance of the tissue through which the electrosurgical output signal is conducted. To correctly model the high frequency response characteristics of the output transformer 36 (FIG. 1), the equivalent circuit 110 must include additional elements to account for the parasitic capacitance characteristics of the power output transformer 36 and the isolation capacitors 50 (FIG. 1). These additional elements include a series shunt resistor ($R_{ser/shunt}$) 130 and a shunt capacitor ($C_{shunt}$) 132 and a series capacitor ($C_{series}$) 134. The series capacitor ($C_{series}$) 134 accounts for the capacitive effects of the isolating capacitors 50 (FIG. 1), and the series shunt resistor ($R_{ser/shunt}$) 130 models the inherent resistive effects of the isolating capacitors. The shunt capacitor ($C_{shunt}$) 132 models the parasitic capacitances that arise between the conductor coils that form the primary winding 38 and the secondary winding 40 (FIG. 1). Similar to the inductors 116, 120, and 124, the capacitors 132 and 134 introduce phase shifts between the currents and the voltages that are present at the primary winding and the secondary winding. In addition, the capacitances store energy and attenuate energy at different frequencies throughout the frequency spectrum. Consequently, some of the input energy delivered by the power supply 70 (FIG. 1) is stored in the capacitors 132 and 134 until that stored energy is discharged during electrosurgery.

The output equivalent circuit 110, shown in FIG. 3, is used to derive a discrete-time function for the output transformer 36 (FIG. 1). The discrete-time function is then used to calculate the output response function of the transformer 36. To proceed in this manner, the value for the resistors 114, 118, 122, and 130, the values for the inductors 116, 120, and 124, and the values for the capacitor 132 are determined experimentally. Any values determined to be negligible are taken as zero when deriving the discrete-time function from the equivalent circuit. In one implementation, the values for the primary leakage resistor 114 and the primary leakage inductor 116 were set as zero, since their contributions were found experimentally to be negligible for the actual output transformer 36 (FIG. 1)

The output voltage simulator 104 (FIG. 2) uses the digital voltage and current signals 54e and 58e as input signals. The approach to arriving at the discrete-time function by use of the equivalent circuit model 110 (FIG. 3) is shown in FIGS. 4-6.

By using standard circuit analysis techniques, the equivalent circuit model 110 yields the continuous-time, frequency-domain function 136 shown in FIG. 4. The continuous-time, frequency-domain function 136 provides the desired voltage output response $V_{out}(s)$ 128 (FIG. 3). The continuous-time, frequency-domain function consists of eleven constants, the input voltage variable $V_{in}(s)$ 126 (FIG. 3) and the input current variable $I_{in}(s)$ 125 (FIG. 3). The values of the eleven constants are calculated from the experimentally determined values for the lumped parameter components of the equivalent circuit 110 (FIG. 3). The input voltage variable $V_{in}(s)$ 126 and the input current variable $I_{in}(s)$ 125 (FIG. 3) are obtained from the digital voltage and current signals 54e and 58e (FIG. 2), respectively. The function 136 shown in FIG. 4 represents the Laplace transform of the equivalent circuit 110 (FIG. 3).

Figure 5:
Figure 6:

The function 136 shown in FIG. 4 is thereafter mathematically transformed into a discrete-time, frequency-domain function 138, shown in FIG. 5, using recognized techniques for transforming continuous-time, frequency-domain functions into discrete-time, frequency-domain functions. Due to the fact that such transformations are not precise mathematical derivations, but instead involve numerical fitting techniques to minimize differences, the transformation shown in FIG. 5 results in twelve new constants rather than the previous eleven constants shown in FIG. 4. A transformation which provides closer numerical minimization might require an even greater number of constants, but will be more complex for computational execution. Conversely, a transformation which provides less close numerical minimization might involve a lesser number of constants, and will be less complex for computational execution. The input and output response variables of the function 138 are discrete values.

The output voltage simulator 104 (FIG. 3) requires that the input variables be in the time domain as opposed to the frequency domain. Thus, a final transformation is required to take the function from the discrete-time, frequency-domain shown in FIG. 5 to the discrete-time, time-domain. As shown in FIG. 6, the final function 139 constitutes the mathematical simulation algorithm which is employed by the output voltage simulator 104 (FIG. 3) to obtain the simulated voltage signal 62 (FIGS. 1 and 2). After this final function 139 is obtained, it is programmed into the array of logic gates which form the output signal simulator 104. Alternatively, the function 139 may be programmed into any device capable of performing programmed digital calculations, although other types of digital calculation devices may not provide the speed and response characteristics that are available from an array of logic gates.

Relating the discrete-time, time-domain function 139 shown in FIG. 6 to samples of the discrete values performed by ADC 96 (FIG. 2), the input samples $V_{in}[n]$ and $I_{in}[n]$ of the function 139 correspond to the filtered digital voltage signal 54e and filtered digital current signal 58e (FIG. 2), respectively. The input samples $V_{in}[n]$ and $I_{in}[n]$ are supplied at the regular and continuously occurring sampling point times [n] at which the ADC 96 (FIG. 2) supplies new values of the filtered digital voltage signal 54e and filtered digital current signal 58e (FIG. 2). The sampling point times [n] are established by the clock 98 (FIG. 2). As is apparent from the function 139, at least three sequentially-occurring input samples (n, n−1, and n−2) of the input samples $V_{in}[n]$ and $I_{in}[n]$ are required to establish initial conditions before the function 139 will produce a meaningful value of $V_{out}[n]$. The value of $V_{out}[n]$ becomes the simulated voltage signal 62 (FIGS. 1 and 2).

The mathematical algorithm represented by the function 139 is based on characteristics of the output transformer 36 and the isolation capacitors 50 (FIG. 1). The accuracy of the simulation using the function 139 will depend on the accuracy and ability to experimentally determine or measure the parasitic and other characteristic values from the actual transformer and isolation capacitors for use in the equivalent circuit 110 (FIG. 3), since the twelve constants in the discrete-time function 139 (FIG. 6) are directly dependent upon these values. The extent of simulation error also relates to the amount of load attached to transformer as the output circuit. In general, the simulation error tends to be lower for lesser output currents from the transformer into smaller loads, and the simulation error tends to be higher for greater output currents from the transformer into larger loads. However, the equivalent circuit model technique (FIGS. 3-6) of deriving a mathematical algorithm for simulating the output voltage has the advantage of providing less error under the circumstances, represented by function 139, where two input signals create one output signal and one of the two input signals is partially caused by the other. The primary current to the transformer is partially caused by the primary voltage and is partially caused by the output load.

The same mathematical algorithm, such as the discrete-time function 139 (FIG. 6), may be programmed and used in each voltage simulator 104 (FIG. 2) of every mass-produced electrosurgical generator if the characteristics among the individual power output transformers in all of the electrosurgical generators are approximately equal. Under such circumstances the need to individually program each simulator with a different mathematical algorithm is avoided. However, if significant variances in parametric values exist from one transformer to the next, the mathematical algorithm may need to be adjusted or re-determined for each individual transformer. In addition, because the loading characteristics may create variances in the simulation error, different mathematical algorithms may be used to simulate the response characteristics over different areas of a load curve. Thus, different simulation algorithms may be employed. Although different mathematical algorithms have been used with respect to the voltage simulator 104 (FIG. 2) as discussed above, the concepts involved in using different mathematical algorithms are also applicable to the current and power simulators 106 and 108 (FIG. 2) discussed below.

Another way of obtaining the simulation algorithm is an iterative numerical comparison of the digital voltage and current signals 54e and 58e (FIG. 2) over a range of load parameters. Iterative numerical comparison technique is a type of system identification technique. System identification techniques are a specific form of adaptive signal processing, and they implement a numerical analysis process in which the observed inputs and outputs of an unknown or poorly-understood system are used to create a transfer function or a discrete-time function of that system. System identification techniques are useful to predict the behavior of the unknown or poorly-known system without first discovering the principles of that system. All that is required to perform this type of system identification is the ability to gather and correlate relevant input and output signals and convert those signals into a form for comparison and manipulation by a microprocessor or computer.

Figure 7:
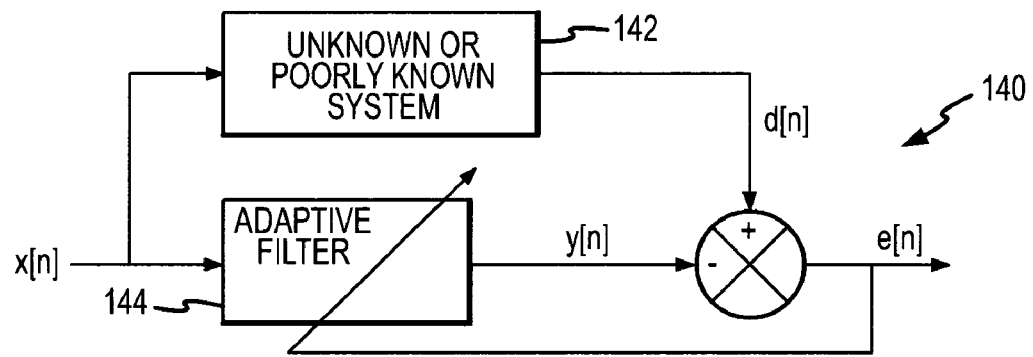
FIG. 7 is a block diagram of an analytical circuit model used in iterative numerical comparison to obtain a simulation algorithm executed by a simulator of the output signal simulation circuit shown in FIG. 2.

FIG. 7 generally illustrates an analytical model 140 which may be used to correlate relevant input and output signals and convert those signals into a form for comparison and manipulation using system identification. The variable x[n] represents a general input signal into the unknown or poorly-known system 142. In the case of the present invention, the system 142 constitutes the output circuit formed by the output transformer 36 and isolation capacitors 50 (FIG. 1). In the analytical model 140, the input variable x[n] represents the digital voltage signal 54e and the digital current signal 58e (FIG. 3), represented as $V_{in}[n]$ and $I_{in}[n]$, respectively. The input variables $V_{in}[n]$ and $I_{in}[n]$ are acted upon by the system 142 in a way which can be characterized and identified by an unknown transfer function, which will be identified by iterative numerical comparison system identification techniques.

When the analytical model 140 is used to obtain the simulated output current 64 (FIGS. 1 and 2), the observed or desired output d[n] is observed and recorded as $I_{out}[n]$. Ultimately once the transfer function has been derived, $I_{out}[n]$ will become the simulated current signal 64 (FIGS. 1 and 2). The system identification technique illustrated by FIG. 7 has been determined experimentally to provide more accurate results for simulating the output current than for simulating the output voltage of the output transformer 36 and the isolation capacitors 50 of the output circuit of the electrosurgical generator 20 (FIG. 1).

The system identification analytical model 140 employs an adaptive response filter 144. The adaptive response filter 144 possesses the constants of equations 146 and 147 shown in FIGS. 8 and 9. Each of these constants is determined simultaneously through the iterative numerical comparison process. Referring to FIG. 7, the input variable x[0] is acted upon initially by both the transfer function of the unknown system 142 and the adaptive response filter 144. The unknown system 142 produces the output variable d[0], and the adaptive response filter 144 produces the output variable y[0]. The output variables d[0] and y[0] are compared with each other to produce the error variable e[0]. Based upon the magnitude of the error variable e[0], the adaptive response filter will "adapt" to the next input variable x[n] through numerical analysis, such as a least mean squares or recursive least squares analysis, and produce new estimates for the constants of the adaptive response filter 144. Through subsequent iterations [n], [n+1], [n+2], etc., the error variable e[n] should approach zero, indicating that the output variable y[n] and the desired output d[n] are approaching equality. When the error signal e[n] approaches 0, the constants implemented by the adaptive response filter 144 have sufficiently converged to the point that the adaptive response filter 144 then represents a reasonable estimation of the true transfer function of the unknown or poorly-known system 142.

The system identification technique described is computationally intensive and is usually the most expeditiously accomplished by the use of known system identification software, such as MATLAB® software and its "System Identification Toolbox." Such software is employed to derive the constraints implemented by the adaptive response filter 144 as well as to perform the iterative numerical comparison.

Performing the iterative numerical comparison begins with gathering experimental data. Signals representative of the primary voltage 44, primary current 46 and the output current 24 (FIG. 1) are gathered in a sampling oscilloscope at a very high sample rate, for example 20 million samples per second. The signals representative of the primary voltage 44, the primary current 46 and the output current 24 are obtained and stored for a range of loads typically experienced during electrosurgery, such as within the range or set of 0, 20, 50, 100, and 500 ohms. For each signal representative of the primary voltage 44 in the primary current 46, the individual signals for each of the impedances in the set are concatenated in order of their load. In this manner, the system is treated as a linear time-invariant system where individual responses are concatenated to represent the overall response. To eliminate window multiplication frequencies that could create an adverse influence, a conventional Hanning window is applied to each signal.

After successfully gathering the experimental data in the described manner, the number of poles and zeros which the system identification software will use to model the transfer function is next selected. As shown in FIGS. 8 and 9, the modeling uses six zeros and six poles, as evidenced by the form of the numerators and denominators in the equations of the discrete-time function. A greater or lesser number of zeros or poles can be used. Adding more zeros and poles produces more complex discrete-time functions, and generally increases the accuracy of the function. Alternatively, removing zeros and poles decreases the complexity of the discrete-time function, but at the expense of its accuracy.

The discrete-time, frequency-domain function 146 shown in FIG. 8 was obtained by use of the system identification toolbox of MATLAB® software in the manner described above. Using a mathematical transformation, the discrete-time function 146 is transformed to the discrete-time, time-domain function 147 shown in FIG. 9. The derived discrete-time function 147 is an accurate and equivalent representation of the true transfer function of the unknown or poorly known system 142 (FIG. 7), which in this example is the output transformer 36 and isolation capacitors 50 of the electrosurgical generator 20 (FIG. 1).

Once the discrete-time, time-domain function 147 is obtained, that function 147 is programmed into the output current simulator 106 (FIG. 2) as a simulation algorithm. As shown in FIG. 2, the simulator 106 executes the simulation algorithm when the digital voltage signal 54e and the digital current signal 58e, (shown in FIG. 9 as $V_{in}[n]$ and $I_{in}[n]$, respectively), are supplied to the simulator 106. A calculation using $V_{in}[n]$ and $I_{in}[n]$ as the independent variables of the derived discrete-time function 147 (FIG. 9) produces the output of $I_{out}[n]$, which is the simulated current signal 64.

Preferably, the simulator 106 is implemented by an array of logic gates which have been programmed to execute the simulation algorithm function 147 (FIG. 9). Other types of digital signal processors could be used in place of the logic gate array, but other types of digital signal processors generally consume more time in executing the simulation algorithm than would normally be consumed by the gate and calculation clocking delays of a logic gate array.

The implementation of the output voltage simulator 104 (FIG. 2) has been described using the equivalent circuit 110 (FIG. 3), while the implementation of the current simulator 106 (FIG. 2) has been described using the discrete-time function 147 (FIG. 9). However, an equivalent circuit may also be derived for use by the current simulator 106 (FIG. 2), although the expression for the output current is more complex than the final function 139 (FIG. 6) obtained for the voltage. Similarly, system identification techniques may also be used by the voltage output simulator 104 (FIG. 2). Shown in FIGS. 10 and 11 are the functions or equations 148 and 149 used to arrive at the simulation algorithm of the voltage output 22 (FIG. 1). Although the system identification voltage functions 148 and 149 are derived from the original current system identification functions 146 and 147 (FIGS. 8 and 9) by straightforward substitutions, the accuracy of the voltage output simulation using system identification is dependent upon the mode of operation of the electrosurgical generator (e.g., cut, blend or coagulation) and the load into which the electrosurgical generator delivers the output power.

In the above discussion of using the mathematical algorithms to simulate the voltage signal 62 and the current signal 64 (FIGS. 1 and 2), the output signal simulation circuit 60

(FIG. 1) is described as operating on an instantaneous sampling basis established by the clock frequency of the clock 98 (FIG. 2). However, it is also possible to calculate time averaged or time integrated values, such as root mean square values, from a set of N number of simulation values that are obtained before the respective discrete-time functions 139 (FIG. 6) and 147 (FIG. 9) are employed to derive the simulated signals 62 and 64. The simulation may be performed using any number of sample points. If the simulations are conducted immediately after obtaining each signal 54e and 58e, then the simulated voltage signal 62 and the simulated current signal 64 will represent an essentially instantaneous voltage signal 22 and an essentially instantaneous current signal 24 (FIG. 1). By obtaining multiple instantaneous simulated output values in succession, a continuum of the voltage and current signals 22 and 24 present on the secondary winding 40 of the output transformer 36 (FIG. 1) is obtained.

As shown in FIG. 2, the power is calculated by the simulator 108 using the instantaneous values of the digital voltage signal 54e and the digital current signal 58e. The instantaneous output power is preferably calculated by obtaining the input power to the transformer from the voltage and current digital signals 54e and 58e and then subtracting out the transformer losses. Alternatively, the instantaneous output power can be calculated by multiplication of the simulated output voltage 62 and the simulated output current 64. The signals 54e, 58e, 62 and 64 are instantaneous signals when developed within each cycle of the clock 98 (FIG. 2). An average power output can be obtained by summing the simulated power output values for N number of values and then dividing by N. Other algorithms for determining root mean square power, apparent power and imaginary power can also be implemented in the simulator 108.

One of the algorithms that can be implemented by the output power simulator 108 is based upon conservation of energy principles wherein the output power of the transformer 36 (FIG. 1) is equal to the input power minus power losses. All power losses, including copper conductor losses, can be accounted for if desired. Accounting only for the core losses, the power losses of the output transformer 36 (FIG. 1) are given by the following expression:

$$k_{mag} \sum_{n=1}^{N} V_{in}^2[n]$$

where $k_{mag}$ is an empirically measured loss factor derived through experimentation, $V_{in}$ is the input voltage 44 applied to the transformer 36 (FIG. 1), and N is the number of samples used in making the power calculation. For an instantaneous output power calculation, N=1. The expression for power losses is based upon negligible values for the primary leakage inductor 116 and the primary leakage resistor 114, and the impedance of the magnetic resistor 118 being small relative to the impedance of the magnetic inductor 120 (FIG. 3). Further, some of the assumptions made for the above power simulation model are based on using the simulated power signal 66 (FIG. 2) as feedback for power control when the current and voltages are both relatively small.

The present invention is equally applicable to simulating the output voltage and output current from any type of transformer of an electrosurgical generator, not just from the output power transformer 36 shown in FIG. 1. For example, most high-voltage output sensors and output current sensors use transformers. The simulation available from the present invention may be employed on such sensors.

Figure 12:
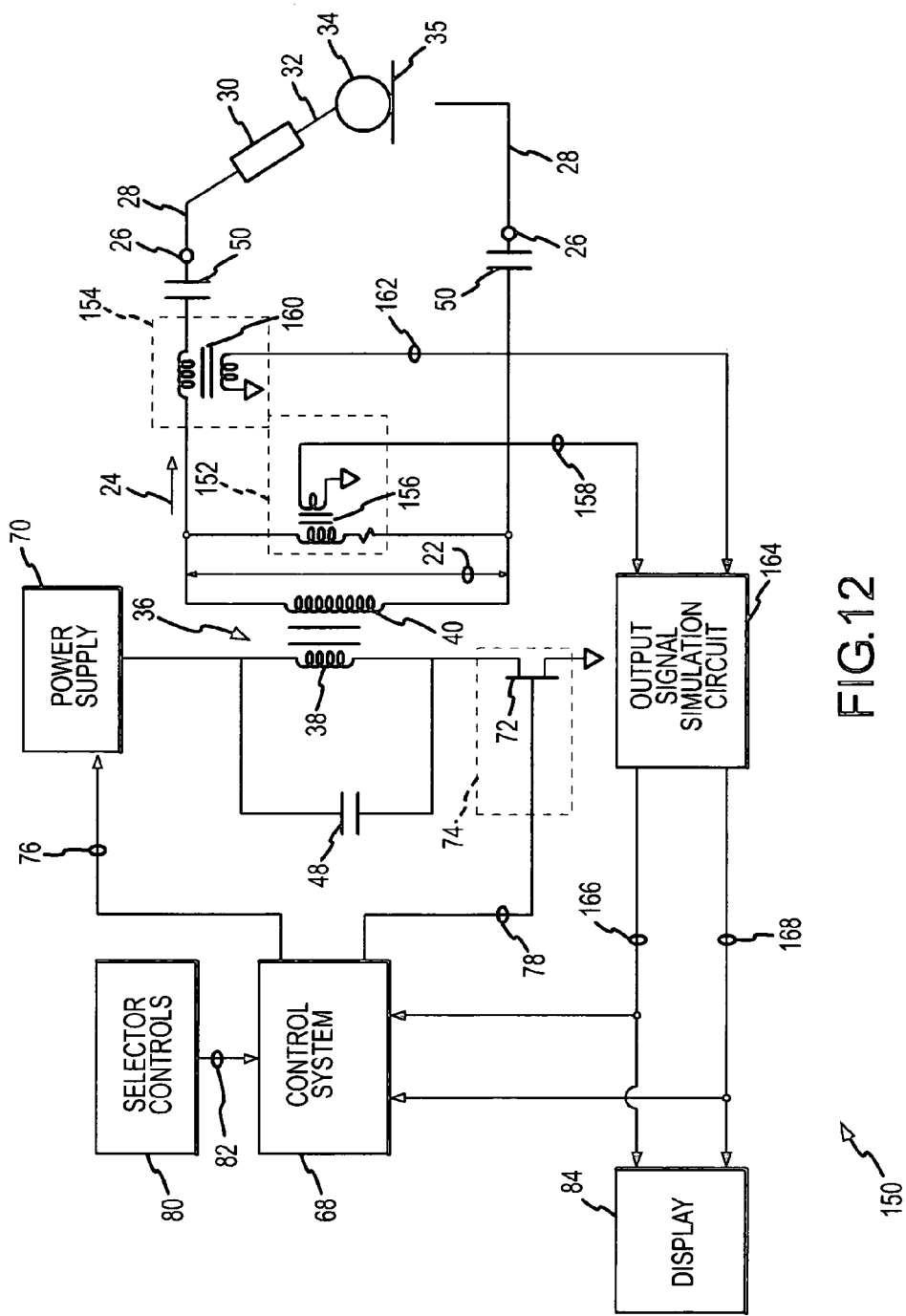
FIG. 12 is a block diagram of another electrosurgical generator which incorporates the present invention.

As shown in FIG. 12, an electrosurgical generator 150 uses many of the same components as have been shown and described in FIG. 1, except that the electrosurgical generator 150 does not sense the output voltage 22 and the output current 24 from the primary winding 38 of the output transformer 36. Instead, the electrosurgical generator 150 uses an output voltage sensor 152 which is connected in parallel with the secondary winding 40 and also uses an output current sensor 154 which is connected in series with the conductor 28 and the secondary winding 40. The voltage sensor 152 uses a transformer 156 to produce a reduced level voltage sense signal 158. Similarly, the output current sensor 154 uses a transformer 160 to develop a current sense signal 162 which represents the output current 24.

Since both of the transformers 156 and 160 are subject to many of the high-frequency high-voltage influences that affect the output transformer 36, those influences combine with the inherent distortions created by an actual transformer to cause the actual characteristics of the sense signals 158 and 162 to depart from those of an ideal transformer. To counter these distortions, the voltage and current sense signals 158 and 162 are supplied to an output signal simulation circuit 164 to provide simulated output signals 166 and 168 which accurately and truly represent the output voltage 22 and the output current 24 which are sensed by the sensors 152 and 154. The output signal simulation circuit 164 corrects for the distortions introduced by the transformers 156 and 160, in a similar manner as has been described above. The simulated output signals 166 and 168 therefore more accurately represent the output voltage and current 22 and 24, and provide an enhanced opportunity for the electrosurgical generator 150 to operate in an improved manner in the very demanding electrosurgical environment where high-voltage and high-frequency signals must be derived accurately and utilized quickly.

Even though the present invention may be employed with separate output voltage and current sensors 152 and 154, as shown in FIG. 12, one of the substantial benefits of the present invention is accurately simulating the output voltage 22 and the output current 24 without connecting sensors on the secondary winding 40 of the output power transformer 36. Instead, by accurately and reliably simulating the output voltage 22 and the output current from signals obtained from the primary winding 38, as shown in FIG. 1, the adverse influences on the output signal formed by the sensors 152 and 154 (FIG. 12) are avoided entirely. The signals obtained from the primary winding are used to reliably simulate the output voltage 22 and output current 24 by correcting for the distortions induced by the output transformer 36 and without inducing further distortions by sensors 152 and 154 (FIG. 12) connected to sense the electrosurgical output signal.

Connecting output voltage and current sensors 152 and 154 (FIG. 12) to the secondary winding of the output transformer has the effects of degrading the quality of the output signal and increasing leakage current, as well as diminishing the available power for use in electrosurgery. However, in those cases where it is desired to separately sense the output voltage and the output current, the present invention provides enhanced and more accurate sense signals because the distortions introduced by the sensing transformer are essentially eliminated by the simulation algorithm.

Using an array of programmable logic gates to implement the mathematical algorithms for simulating the output signals offers a substantial advantage in quickly deriving the simulated signals. The array of logic gates has the ability to calculate the simulated signals rapidly, with any delays in the calculation consumed only by gate and clocking delays within the logic gate array. Reducing the time required to simulate the output signals makes the simulated output signals available on an almost instantaneous basis. The temporal presence of the simulated output signal is usually a significant advantage in obtaining more responsive control from the electrosurgical generator.

The significance of these and other improvements and advantages will become apparent upon gaining a full appreciation of the ramifications and improvements of the present invention. Preferred embodiments of the invention and many of its improvements have been described with a degree of particularity. The detail of the description is of preferred examples of implementing the invention. The detail of the description is not necessarily intended to limit the scope of the invention. The scope of the invention is defined by the following claims.

The invention claimed:

1. An electrosurgical generator which supplies a high-frequency, high-voltage electrosurgical output signal to tissue to create an electrosurgical effect, the electrosurgical generator including a transformer having a primary winding and a secondary winding, the secondary winding conducting the electrosurgical output signal, the transformer inducing voltage and current signals between the primary and secondary windings that are distorted relative to one another due to inherent characteristics of the transformer at the high frequency and high-voltage of the electrosurgical output signal, the electrosurgical generator further comprising:
    a primary voltage sensor connected to the primary winding to supply a primary voltage sense signal related to the voltage across the primary winding;
    a primary current sensor connected to the primary winding to supply a primary current sense signal related to the current conducted through the primary winding; and
    a simulation circuit receptive of the primary voltage sense signal and the primary current sense signal, the simulation circuit executing a mathematical simulation algorithm to transform at least one of the primary voltage and current sense signals into at least one simulated signal which accurately represents an actual value of the voltage or current of the electrosurgical output signal conducted by the secondary winding of the transformer, the transformation of the one of the primary voltage and current sense signals by the simulation algorithm correcting the distortion introduced by the transformer.

2. An electrosurgical generator as defined in claim 1, wherein:
    the simulation algorithm executed by the simulation circuit responds to both the primary voltage and current sense signals to supply the one simulated signal.

3. An electrosurgical generator as defined in claim 1, wherein:
    the simulation circuit executes at least one simulation algorithm which responds to both the primary voltage and current sense signals to supply simulated signals which accurately represent accurate values of both the voltage and current of the electrosurgical output signal.

4. An electrosurgical generator as defined in claim 1, wherein:
    the simulation circuit responds to both the primary voltage and current sense signals and executes one simulation algorithm to supply one simulated signal which accurately represents the actual value of the voltage of the electrosurgical output signal conducted by the secondary winding of the transformer and executes another simulation algorithm which accurately represents the actual value of the current of the electrosurgical output signal.

5. An electrosurgical generator as defined in claim 4, wherein:
    one of the simulation algorithms is derived from a lumped parameter, equivalent circuit model over a range of load parameters representative of the electrosurgical loads to which the electrosurgical output signal is normally applied; and
    the other of the simulation algorithms is derived from iterative numerical comparison of the primary voltage and current sensed signals and the voltage and current of the electrosurgical output signal over a range of load parameters representative of the electrosurgical loads to which the electrosurgical output signal is normally applied.

6. An electrosurgical generator as defined in claim 1, wherein:
    the simulation circuit comprises an array of logic gates which receive the primary voltage and current sense signals and execute the simulation algorithm in response to the primary voltage and current sense signals.

7. An electrosurgical generator as defined in claim 1, wherein:
    the primary current and voltage sensors supply the primary current and voltage sense signals as analog signals, respectively; and further comprising:
    an analog-to-digital converter for converting the primary voltage and current sense analog signals into primary voltage and current sense digital signals, respectively; and wherein:
    the simulation circuit comprises an array of logic gates which receive the primary voltage and current sense digital signals and execute the simulation algorithm directly in response to the primary voltage and current sense digital signals.

8. An electrosurgical generator as defined in claim 1, wherein:
    the simulation circuit comprises an array of logic gates which am programmed to execute the simulation algorithm.

9. An electrosurgical generator as defined in claim 1, wherein:
    the transformer comprises part of a sensor, the secondary winding of the transformer conducts the electrosurgical output signal, and the primary winding of the transformer conducts at least one of the primary voltage and current sense signals.

10. An electrosurgical generator as defined in claim 1, wherein:
    the transformer comprises a power output transformer of the electrosurgical generator, the secondary winding of the power output transformer supplies the electrosurgical output signal, and the primary winding of the power output transformer conducts an input voltage and an input current applied to induce the electrosurgical output signal from the secondary winding.

11. An electrosurgical generator as defined in claim 10, wherein:
    the primary voltage sensor comprises a portion of the primary winding.

12. An electrosurgical generator as defined in claim 10, wherein:
    the power output transformer comprises part of a power output circuit of the electrosurgical generator which also includes isolating capacitors connected in series with the secondary winding; and the simulation circuit is responsive to both the primary voltage sense signal and the primary current sense signal and executes at least one mathematical simulation algorithm to transform the primary voltage and current sense signals into at least one simulated signal which accurately represents an actual value of voltage or current of the electrosurgical output signal conducted by the power output circuit, the simulation algorithm correcting for distortion introduced by the power output transformer and for any signal anomalies introduced by the isolation capacitors.

13. An electrosurgical generator as defined in claim 12, wherein:
the simulation algorithm is derived from a lumped parameter, equivalent circuit model of the power output circuit over a range of load parameters representative of the electrosurgical loads to which the electrosurgical output signal is normally applied.

14. An electrosurgical generator as defined in claim 13, wherein:
the simulation algorithm derived from the lumped parameter, equivalent circuit model supplies the simulated signal representative of voltage of the electrosurgical output signal.

15. An electrosurgical generator as defined in claim 12, wherein the simulation algorithm comprises a mathematical function which has a first variable formed by the primary-voltage sense signal, a second variable formed by the primary current sense signal, and a set of coefficients determined from an equivalent circuit model of the power output circuit.

16. An electrosurgical generator as defined in claim 12, wherein:
the simulation algorithm is derived from iterative numerical comparison of the primary voltage and current sense signals and voltage and current of the electrosurgical output signal over a range of load parameters representative of the electrosurgical loads to which the electrosurgical output signal is normally applied.

17. An electrosurgical generator as defined in claim 12, wherein the simulation algorithm comprises a mathematical function which has a first variable formed by the primary voltage sense signal, a second variable formed by the primary current sense signal, and a set of coefficients determined by an iterative numerical comparison of the primary voltage and current sense signals and voltage and current of the electrosurgical output signal over a range of load parameters representative of the electrosurgical loads to which the electrosurgical output signal is normally applied:

18. An electrosurgical generator as defined in claim 12, wherein:
the simulation circuit executes at least one simulation algorithm which supplies a simulated signal that accurately represents the power of the electrosurgical output signal.

19. An electrosurgical generator as defined in claim 18, wherein:
the simulated signal supplied represents a mathematical product of accurate values of the voltage and current of the electrosurgical output signal.

20. An electrosurgical generator as defined in claim 18, wherein:
the simulated signal supplied represents a mathematical product of the primary voltage sense signal and the primary current sense signal from which is subtracted a value representative of core losses of the transformer.

21. A method of accurately simulating at least one of voltage or current of an electrosurgical output signal conducted by a secondary winding of a transformer which has inherent characteristics that distort the respective values of the current and voltage induced between a primary winding and the secondary winding of the transformer, comprising:
sensing a primary voltage across the primary winding of the transformer and supplying a primary voltage sense signal related to the voltage across the primary winding;
sensing a primary current conducted through the primary winding of the transformer and supplying a primary current sense signal related to the current conducted through the primary winding;
using a computation circuit to execute a mathematical simulation algorithm in response to the primary voltage and current sensed signals to transform at least one of the primary voltage and current sensed signals into at least one simulated signal which accurately represents an actual value of the voltage or current of the electrosurgical output signal conducted by the secondary winding of the transformer; and
compensating for the distortion induced by the transformer in the mathematical simulation algorithm.

22. A method as defined in claim 21, further comprising:
executing the simulation algorithm to supply simulated signals which accurately represent actual values of both the voltage and current of the electrosurgical output signal.

23. A method as defined in claim 21, further comprising:
executing one simulation algorithm to supply one simulated signal which accurately represents the actual value of the voltage of the electrosurgical output signal conducted by the secondary winding of the transformer; and
executing another simulation algorithm to supply another simulated signal which accurately represents the actual value of the current of the electrosurgical output signal.

24. A method as defined in claim 23, further comprising:
deriving one of the simulation algorithms from a lumped parameter, equivalent circuit model over a range of load parameters representative of the electrosurgical loads to which the electrosurgical output signal is normally applied; and
deriving the other of the simulation algorithms from iterative numerical comparison of the primary voltage and current sensed signals and the voltage and current of the electrosurgical output signal over the range of load parameters representative of the electrosurgical loads to which the electrosurgical output signal is normally applied.

25. A method as defined in claim 21, further comprising:
executing the simulation algorithm in an array of logic gates in response to the primary voltage and current sense signals.

26. A method as defined in claim 21 wherein the transformer comprises part of a sensor and the primary winding of the transformer conducts at least one of the primary voltage and current sense signals.

27. A method as defined in claim 21, wherein the transformer comprises a power output transformer of the electrosurgical generator, the secondary winding of the power output transformer supplies the electrosurgical output signal, and the primary winding of the power output transformer conducts an input voltage and an input current applied to induce the electrosurgical output signal from the secondary winding.

28. A method as defined in claim 27, wherein the power output transformer comprises part of a power output circuit of the electrosurgical generator which also includes isolating capacitors connected in series with the secondary winding.

29. A method as defined in claim 28, further comprising:
deriving the simulation algorithm from a lumped parameter, equivalent circuit model of the power output circuit over a range of load parameters representative of the electrosurgical loads to which the electrosurgical output signal is normally applied.

30. A method as defined in claim 28, further comprising:
forming the simulation algorithm as a mathematical function which supplies the simulated signal from a first variable formed by the primary voltage sense signal and from a second variable formed by the primary current sense signal and a set of coefficients determined from one of either an equivalent circuit model of the transformer or iterative numerical comparison of the voltage and current signals from the primary winding and the voltage and current of the electrosurgical output signal over a range of load parameters representative of the electrosurgical loads to which the electrosurgical output signal is normally applied.

31. A method as defined in claim 21, further comprising:
deriving the simulation algorithm from iterative numerical comparison of the primary voltage and current sense signals and the voltage and current of the electrosurgical output signal over a range of load parameters representative of the electrosurgical loads to which the electrosurgical output signal is normally applied.

32. A method as defined in claim 21, further comprising:
forming the mathematical algorithm as a mathematical function which supplies the simulated signal from a first variable formed by the primary voltage sense signal and a second variable formed by the primary current sense signal and a set of coefficients determined by an iterative numerical comparison of the primary voltage and current sense signals and the voltage and current of the electrosurgical output signal over a range of load parameters representative of the electrosurgical loads to which the electrosurgical output signal is normally applied.

33. A method as defined in claim 21, further comprising:
executing at least one simulation algorithm which supplies a simulated signal that accurately represents the power of the electrosurgical output signal.

34. A method as defined in claim 33, wherein the simulated signal supplied represents a mathematical product of accurate values of the voltage and current of the electrosurgical output signal.

35. A method as defined in claim 33, wherein the a simulated signal supplied represents a mathematical product of the primary voltage sense signal and the primary current sense signal from which is subtracted a value representative of core losses of the transformer.

\* \* \* \* \*

UNITED STATES PATENT AND TRADEMARK OFFICE
CERTIFICATE OF CORRECTION

PATENT NO. : 7,736,358 B2
APPLICATION NO. : 11/541880
DATED : June 15, 2010
INVENTOR(S) : Ronald B. Shores and Brian C. Stuebe It is certified that error appears in the above-identified patent and that said Letters Patent is hereby corrected as shown below:

Column 18, claim 8, line 40, delete "am" and substitute -- are --.

Column 19, claim 15, lines 27-28, delete "primary-voltage" and substitute -- primary voltage --.

Column 19, claim 17, line 48, delete "applied:" and substitute -- applied. --.

Column 22, claim 35, line 20, delete "a".

Signed and Sealed this
Twenty-second Day of February, 2011

David J. Kappos
*Director of the United States Patent and Trademark Office*